United States Patent
Dave et al.

(10) Patent No.: US 9,055,742 B2
(45) Date of Patent: Jun. 16, 2015

(54) HERBICIDE GRANULES WITH BUILT-IN ADJUVANT

(75) Inventors: Hiteshkumar Dave, Carmel, IN (US); Lei Liu, Carmel, IN (US); David G. Ouse, Indianapolis, IN (US); Richard K. Mann, Franklin, IN (US); Raymond E. Boucher, Jr., Lebanon, IN (US); Deborah G. Shatley, Lincoln, CA (US); Toshiya Ogawa, San Ramon, CA (US); Alan E. Haack, Roseville, CA (US)

(73) Assignee: Dow AgroSciences LLC, Indianapolis, IN (US)

(*) Notice: Subject to any disclaimer, the term of this patent is extended or adjusted under 35 U.S.C. 154(b) by 4 days.

(21) Appl. No.: 13/529,455

(22) Filed: Jun. 21, 2012

(65) Prior Publication Data

US 2013/0023414 A1    Jan. 24, 2013

Related U.S. Application Data

(60) Provisional application No. 61/499,887, filed on Jun. 22, 2011.

(51) Int. Cl.
*A61K 9/14* (2006.01)
*A01N 25/12* (2006.01)

(52) U.S. Cl.
CPC .................................. *A01N 25/12* (2013.01)
USPC ........ 424/489; 424/405; 424/407; 504/116.1; 504/130

(58) Field of Classification Search
CPC ............................... A01N 25/12; A01N 39/02
USPC ................ 424/405, 409, 489; 504/116.1, 130
See application file for complete search history.

(56) References Cited

U.S. PATENT DOCUMENTS

| | | | |
|---|---|---|---|
| 2007/0184980 A1 | 8/2007 | Roberts et al. | |
| 2008/0254983 A1 | 10/2008 | Panayi et al. | |
| 2009/0062127 A1 | 3/2009 | Liu | |
| 2009/0069346 A1* | 3/2009 | Ishihara et al. | 514/256 |
| 2010/0304967 A1 | 12/2010 | Kotzian | |
| 2011/0098181 A1 | 4/2011 | Mann et al. | |
| 2011/0136667 A1* | 6/2011 | Turner et al. | 504/128 |

FOREIGN PATENT DOCUMENTS

| | | | |
|---|---|---|---|
| CN | 102047877 A | * | 5/2011 |
| EP | 307502 A1 | | 3/1989 |

OTHER PUBLICATIONS

Ntanos et al., "Barnyardgrass (*Echinochloa crus-galli*) Control in Water-Seeded Rice (*Oryza sativa*) with Cyhalofop butyl", 2000, Weed Technology, vol. 14, issue 2, pp. 383-388.
U.S. Appl. No. 13/529,236, filed Jun. 21, 2012 (Published as U.S. 2012-0329651-A1).

* cited by examiner

*Primary Examiner* — Ali Soroush

(74) *Attorney, Agent, or Firm* — Michael R. Asam; Meunier Carlin & Curfman, LLC

(57) ABSTRACT

Provided herein are herbicide granules containing non-petroleum derived built-in adjuvant.

19 Claims, No Drawings

HERBICIDE GRANULES WITH BUILT-IN ADJUVANT

CROSS REFERENCE TO RELATED APPLICATIONS

This application claims the benefit of U.S. Provisional Application No. 61/499,887, filed Jun. 22, 2011, the entirety of which is incorporated herein by reference.

FIELD

This invention concerns granules containing a grass-active herbicide and non-petroleum derived built-in adjuvant. Such granules exhibit improved herbicidal efficacy on grass weeds in flooded paddy rice applications.

BACKGROUND

Agrochemical formulations are generally designed based on customer needs and the physiochemical properties of the active ingredients such as, for example, the solubility of the active ingredient in water or non-aqueous solvents. There are two major categories of formulations, solid formulations and liquid formulations.

Granule (GR) products containing agricultural active ingredients represent one class of solid formulations that are widely used because of their handling safety compared to liquid formulations and the advantages they offer with regard to cost savings in packaging and transportation. Granule formulations are similar to powder or dust formulations except that the granule particles are larger (average particle size generally greater than about 100 micrometers) than the particles in powders or dusts (average particle size generally less than about 100 micrometers) and therefore present less of a respiratory hazard. Granule products are generally produced from powders and may be used for insect, weed, fungal pathogen and nematode control and are often used in soil and aquatic environments. Because of the particle weight, granules used in aerial applications may pose a reduced hazard from off-target drift compared to aerial liquid spray applications.

Active ingredients, in the form of solids or liquids, may be formulated as granules and include insecticides, herbicides, fungicides, nematicides and plant growth regulators. Granule formulations usually contain a relatively small amount of the active ingredient since the granules are frequently not further diluted with a carrier solvent such as water prior to use, but are instead applied directly to the area of interest, such as for example, soil or water. Once applied, the active ingredient contained in the granule is released to the area of application, typically upon exposure to water.

Agricultural granules containing active ingredients may also contain solid inert ingredients that serve as a diluent and/or carrier and may also help maintain the granules in a stable, solid state. These solid inert ingredients may include, for example, clays, starches, silicas, sulphates, chlorides, lignosulfonates, carbohydrates such as dextrines, alkylated celluloses, xanthum gums and guaseed gums, and synthetic polymers such as polyvinyl alcohols, sodium polyacrylates, polyethylene oxides, polyvinylpyrrolidones and urea/formaldehyde polymers like PergoPak M® (registered trademark of Albemarle Corporation). The active ingredient(s) contained in a granule may be melted into a liquid, dissolved in a solvent or dispersed in a liquid, which may then be sprayed onto or absorbed into the solid inert ingredients. In the absence of effective solid inert ingredients, dry granules may be physically unstable and, in the case of solid particles, slowly breakdown forming a dust or powder or, in the case of granules containing liquid built-in adjuvants, slowly breakdown forming large liquid droplets as a result of Ostwald Ripening. Many solid inert ingredients used in agricultural granule formulations generally have good water solubility or dispersibility.

Adjuvants are important components of granules and are defined as substances which can increase the biological activity of the active ingredient, but are themselves not significantly biologically active. Adjuvants assist with the effectiveness of the active ingredient such as, for example, by improving the delivery and uptake of an herbicide into a target weed plant leading to improved biological control.

Adjuvants, in the form of solids or liquids, can be added directly to a formulated agricultural product, such as a granule, to provide improved performance of the product upon application. Commonly used adjuvants may include, for example, surfactants, spreaders, petroleum and plant derived oils and solvents, and wetting agents. Examples of commonly used adjuvants include, but are not limited to, paraffin oil, horticultural spray oils (e.g., summer oil), methylated rape seed oil, methylated soybean oil, highly refined vegetable oil and the like, polyol fatty acid esters, polyethoxylated esters, ethoxylated alcohols, alkyl polysaccharides and blends, amine ethoxylates, sorbitan fatty acid ester ethoxylates, polyethylene glycol esters, organosilicone based surfactants, ethylene vinyl acetate terpolymers, ethoxylated alkyl aryl phosphate esters and the like. These and other adjuvants are described in the "*Compendium of Herbicide Adjuvants, 9th Edition*," edited by Bryan Young, Dept. of Plant, Soil and Agricultural Systems, Southern Illinois University MC-4415, 1205 Lincoln Drive, Carbondale, Ill. 62901.

The term "built-in adjuvant" refers to one or more adjuvants that have been added to a particular formulation, such as a granule or liquid formulation, at the manufacturing stage of the product, rather than at the point of use of the product such as, for example, to a spray solution. The use of built-in adjuvants simplifies the use of agrochemical products for the end-user by reducing the number of ingredients that must be individually measured and applied.

Rice is an important cereal crop grown in many parts of the world and is cultivated under both wet and dry conditions. Control of weeds in rice is very important in order to maintain high levels of agricultural productivity. Use of herbicide granules for weed control in flooded paddy rice is a very common agronomic practice in many rice growing regions. New herbicide granule products that offer improved performance relative to current products are needed.

Cyhalofop-butyl, (2R)-2-[4-(4-cyano-2-fluorophenoxy)phenoxy]propanoic acid (CAS #122008-78-0), is a member of the aryloxyphenoxypropionic acid class of herbicides which are known in the art as the fop herbicides and is used to control grass weeds in rice. Cyhalofop-butyl is marketed as Clincher® herbicide (registered trademark of Dow AgroSciences LLC) and is sold in granule (GR), oil in water (EW) and emulsifiable concentrate (EC) formulations and exhibits good selectivity to rice when used in both dry land and flooded paddy applications.

Existing commercial granule formulations of cyhalofop-butyl contain solid inert ingredients such as potassium chloride, clay or starch combined with built-in adjuvants derived from petroleum such as, for example, aromatic solvents. These built-in adjuvants consist of a maximum of from about 15 to about 20 percent by weight relative to the total weight of the cyhalofop-butyl granule in currently marketed products. The use of petroleum based built-in adjuvants in current granule products can limit the biological performance of cyhalofop-butyl herbicide due to a minimal herbicidal adjuvant effect.

The present invention provides an improvement to existing granules containing grass-active herbicides by the use of non-petroleum derived built-in adjuvants and thereby offer improved herbicidal efficacy on weeds in flooded paddy rice applications.

SUMMARY

The present invention concerns an herbicide granule containing a built-in adjuvant which comprises:
a) an aryloxyphenoxypropionic acid herbicide comprising, with respect to the total composition, from about 5 grams active ingredient per kilogram (gai/kg) to about 50 gai/kg;
b) a non-petroleum derived built-in adjuvant comprising, with respect to the total composition, from about 20 g/kg to about 200 g/kg;
c) a water soluble solid carrier comprising, with respect to the total composition, from about 700 g/kg to about 950 g/kg; and
d) a surfactant comprising, with respect to the total composition, from about 1 g/kg to about 50 g/kg;
wherein the weight ratio of the herbicide to the non-petroleum derived built-in adjuvant is from about 1:3 to about 1:40.

Another aspect of the present invention concerns a method of controlling undesirable vegetation in an aquatic environment which comprises broadcasting or adding the herbicide granule to an aquatic environment either before emergence or after emergence of the undesirable vegetation.

DETAILED DESCRIPTION

Agricultural active ingredients that have low water solubility can sometimes be difficult to effectively apply to crops to eliminate pests. This situation is particularly challenging when the active ingredients are not applied directly to plant foliage such as, for example, when herbicide granule products are used to control weeds in flooded paddy rice. Herbicide granules applied to flooded paddy rice are normally added directly to the water in the paddy rice and have very little direct contact with plant foliage during application. Cyhalofop-butyl is an herbicidal active ingredient that when applied to water in a granule, requires the use of a built-in adjuvant to provide the necessary delivery and uptake of the herbicide into the target weeds and expression of acceptable levels of weed control. Cyhalofop-butyl granules that are currently marketed for the control of weeds in flooded paddy rice contain petroleum derived built-in adjuvants such as, for example, aromatic solvents or oils like ditridecyl phthalate.

Cyhalofop-butyl granules that contain non-petroleum derived built-in adjuvants such as, for example, plant-derived methylated seed oils and vegetable oil concentrates have surprising been found to offer improved weed control in aquatic environments such as, for example, flooded paddy rice when compared on a grams active ingredient per hectare (gai/ha) basis to cyhalofop-butyl granules containing petroleum derived adjuvants. The improved weed control is dependent on the weight ratio of the herbicide active ingredient to the non-petroleum derived built-in adjuvant contained in the granule.

The granule of the present invention is comprised of an aryloxyphenoxypropionic acid herbicide active ingredient, a non-petroleum derived built-in adjuvant, a water soluble solid carrier and a surfactant.

The aryloxyphenoxypropionic acid herbicide active ingredient of the present invention may include, but is not limited to, cyhalofop-butyl, fenoxaprop-ethyl, fluazifop-P-butyl, haloxyfop-methyl, haloxyfop-R-methyl, metamifop, propaquizafop, quizalofop-P-ethyl and quizalofop-P-tefuryl. Preferred aryloxyphenoxypropionic acid herbicide active ingredients of the present invention include cyhalofop-butyl, fenoxaprop-ethyl, haloxyfop-methyl, haloxyfop-R-methyl and metamifop. The aryloxyphenoxypropionic acid herbicide active ingredient of the present invention comprises, with respect to the total composition, from about 5 gai/kg to about 50 gai/kg, preferably from about 10 gai/kg to about 30 gai/kg.

The non-petroleum derived built-in adjuvant of the present invention may be in the form of one or more of a naturally derived water immiscible liquid or solid, and a naturally or partially naturally derived non-ionic surfactant. Water immiscible liquids or solids that may be used as the non-petroleum derived built-in adjuvant of the present invention generally have less than about 1 volume percent solubility in water and may include one or more of a plant, algae or animal derived oil such as, but not limited to, seed oils, vegetable oils, animal oils and esters thereof. Naturally or partially naturally derived non-ionic surfactants that may be used as built-in adjuvants of the present invention include, but are not limited to, polyol fatty acid esters, polyethoxylated naturally derived esters, polyethoxylated naturally derived alcohols, alkyl polysaccharides such as alkyl polyglycosides and blends thereof, fatty acid derived amine ethoxylates, sorbitan fatty acid ester ethoxylates and sucrose esters of fatty acids.

Preferred non-petroleum derived built-in adjuvants may include one or more plant derived oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like; $C_1$-$C_{10}$ esters of plant derived oils such as methylated seed oils like methyl soyate, 2-ethyl hexyl stearate, n-butyl oleate, isopropyl myristate, propylene glycol dioleate and the like; polyol fatty acid esters; polyethoxylated esters derived from plant derived oils; polyethoxylated alcohols derived from plant derived oils; alkyl polysaccharides such as alkyl polyglycosides and blends thereof; amine ethoxylates derived from plant derived oils; sorbitan fatty acid ester ethoxylates; and sucrose esters of fatty acids. The non-petroleum derived built-in adjuvant of the present invention comprises, with respect to the total composition, from about 20 g/kg to about 200 g/kg, preferably from about 50 g/kg to about 180 g/kg and most preferably from about 50 g/kg to about 150 g/kg.

The weight ratio of the herbicide active ingredient and the non-petroleum derived built-in adjuvant of the present invention has unexpectedly been found to affect the herbicidal efficacy of the granule when used to control weeds in paddy rice. The weight ratio of the herbicide active ingredient to the non-petroleum derived built-in adjuvant offers improved herbicidal efficacy in the range from about 1:3 to about 1:40, and most preferably from about 1:4 to about 1:40.

The water soluble solid carrier of the present invention may include one or more of a salt of an inorganic or organic acid, a lignosulfonate, a carbohydrate, a fertilizer, a water soluble modified cellulose, a natural gum and a synthetic polymer. Suitable salts of inorganic or organic acids may include alkali metal, magnesium, calcium or ammonium salts of inorganic and organic acids such as hydrochloric acid, sulphuric acid, nitric acid, carbonic acid or acetic acid. Suitable solid carbohydrates may include, for example, glucose, fructose, sucrose, trehalose, lactose and maltose, dextrines, starches and water soluble modified starches. Suitable modified celluloses may include, for example, water soluble alkylated and carboxyalkylated celluloses. Suitable natural gums may include, for example, guar gums, xanthum gums and guarseed gums, and the like. Suitable synthetic polymers may include, for example, polyvinyl alcohols, sodium polyacrylates, polyethylene oxides and polyvinylpyrrolidones.

Preferred water soluble solid carriers of the present invention may include salts of inorganic acids such as, for example, potassium chloride, potassium sulfate, calcium carbonate and sodium sulfate, fertilizers such as, for example, ammonium sulfate and urea, and lignosulfonates such as, for example, calcium lignosulfonate and sodium lignosulfonate. The water soluble solid carrier of the present invention comprises, with respect to the total composition, from about 700 g/kg to about 950 g/kg.

The surfactant of the present invention may be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(octyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; and mixtures thereof. The surfactant of the present invention comprises, with respect to the total composition, from about 1 g/kg to about 50 g/kg.

In a typical procedure for preparing the granule of the present invention a homogeneous oil phase is prepared by mixing together the aryloxyphenoxypropionic acid herbicide active ingredient, the non-petroleum derived built-in adjuvant and the surfactant, optionally with the use of heat as needed. The oil phase is then combined with the granular solid carrier and mixed well to provide the granule of the present invention.

An example of an herbicide granule of the present invention containing a non-petroleum derived built-in adjuvant comprises:
 a) an aryloxyphenoxypropionic acid herbicide active ingredient comprising, with respect to the total composition, from about 5 gai/kg to about 50 gai/kg of cyhalofop-butyl;
 b) a non-petroleum derived built-in adjuvant comprising, with respect to the total composition, from about 20 g/kg to about 200 g/kg of methyl soyate;
 c) a water soluble solid carrier comprising, with respect to the total composition, from about 500 g/kg to about 950 g/kg of potassium chloride; and
 d) a surfactant comprising, with respect to the total composition, from about 1 g/kg to about 50 g/kg of sodium dioctyl sulfosuccinate;
wherein the weight ratio of cyhalofop-butyl to methyl soyate is from about 1:3 to about 1:40.

Another aspect of the present invention concerns a method of controlling undesirable vegetation by broadcasting or adding the herbicide granule of the present invention into an aquatic environment such as rice paddys, ponds, lakes and streams and the like for the control of undesirable vegetation. In this aspect, a herbicidally effective amount of the herbicide granules is applied to an area of water to provide suitable control of undesirable vegetation. The herbicide granule of the present invention is particularly useful for the control of grass weeds in flooded rice paddys or fields and offers improved herbicidal performance relative to current granule products that contain petroleum derived adjuvants and are used to control grass weeds in flooded rice paddys or fields.

Granule formulations can be produced using one or more of the following processing methods: (1) pan granulation, (2) mixing agglomeration, (3) extrusion granulation, (4) fluid bed granulation or (5) spray drying granulation. The physicochemical properties of the active ingredient and additives are important to consider when choosing a process to use. G. A. Bell and D. A. Knowles in, "Chemistry and Technology of Agrochemical Formulations," D. A. Knowles, editor, (Kluwer Academic Publishers, 1998), pages 41-114, describe the types of granules used in agricultural chemical formulations and provide many references to the production of these solid formulations.

In addition to the compositions set forth above, the present invention also embraces compositions containing one or more additional pesticide active ingredients, plant growth regulators or safeners that are added to the granule of the present invention. These pesticide active ingredients, plant growth regulators and safeners may include one or more of an herbicide, an insecticide, a fungicide, a plant growth regulator or an herbicide safener.

Suitable herbicides that may be added to the granule of the present invention include clodinafop-propargyl, clethodim, cycloxydim, diclofop-methyl, fenoxaprop-ethyl+isoxidifen-ethyl, pinoxaden, profoxydim, propaquizafop, quizalofop-P-ethyl, quizalofop-P-tefuryl, sethoxydim, tepraloxydim, tralkoxydim, 2,4-D esters and salts, 2,4-MCPA, 2,4-MCPA esters and salts, acetochlor, acifluorfen, alachlor, amidosulfuron, aminopyralid, aminotriazole, ammonium thiocyanate, anilifos, azimsulfuron, benfuresate, bensulfuron-methyl, bentazon, bentazone-sodium, benthiocarb, benzobicyclon, benzofenap, bifenox, bispyribac-sodium, bromobutide, butachlor, cafenstrole, carfentrazone-ethyl, chlorimuron, chlorpropham, cinosulfuron, clomazone, clomeprop. clopyralid, cloransulam-methyl, cyclosulfamuron, cumyluron, daimuron, diclosulam, diflufenican, dimepiperate, dimethametryn, diquat, dithiopyr, EK2612, EPTC, esprocarb, ET-751, ethoxysulfuron, ethbenzanid, fenoxasulfone, fentrazamide, flazasulfuron, florasulam, fluazifop, flucetosulfuron, flufenacet, flufenpyr-ethyl, flumetsulam, flumioxazin, flupyrsulfuron, fluoroxypyr, fluoroxypyr esters and salts, fomesafen, foramsulfuron, glufosinate, glufosinate-P, glyphosate, halosulfuron-methyl, imazamethabenz, imazamox, imazapic, imazapyr, imazaquin, imazethapyr, imazosulfuron, indanofan, ioxynil, ipfencarbazone, MCPB, mefenacet, mesosulfuron, mesotrione, metazosulfuron, metolachlor, metosulam, metsulfuron, molinate, monosulfuron, MSMA, orthosulfamuron, oryzalin, oxadiargyl, oxadiazon, oxazichlomefone, oxyfluorfen, pendimethalin, penoxsulam, pentoxazone, pethoxamid, picloram, piperophos, pretilachlor, primisulfuron, prohexadione-calcium, propachlor, propanil, propisochlor, propyrisulfuron, prosulfuron, pyrabuticarb, pyraclonil, pyrazogyl, pyrazolynate, pyrazosulfuron-ethyl, pyrazoxyfen, pyribenzoxim, pyridate, pyriftalid, pyriminobac-methyl, pyrimisulfan, pyroxsulam, quinoclamine, quinclorac, S-3252, simazine, simetryne, s-metolachlor, sulcotrione, sulfentrazone, sulfosate, tefuryltrione, thenylchlor, thiazopyr, thiobencarb, triclopyr esters and salts, triafamone, trifluralin, trinexapac-ethyl, tritosulfuron and compounds of the following generic structures and their derivatives as disclosed in U.S. Pat. No. 7,314,849 B2 and U.S. Pat. No. 7,300,907 B2

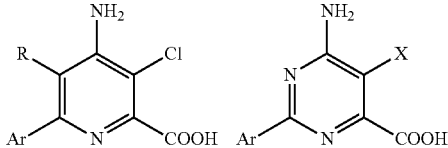

wherein Ar is a polysubstituted phenyl group and R is H or halo and X is halo. Especially suitable herbicides that may be added to the granule of the present invention include penoxsulam and bensulfuron-methyl.

Suitable insecticides that may be added to the granule of the present invention include abamectin, acephate, acetamiprid, acrinathrin, alpha-cypermethrin, alpha-endosulfan, azadirachtin, azinphos-ethyl, azinphos-methyl, bendiocarb, benfuracarb, bensultap, beta-cyfluthrin, beta-cypermethrin, bifenthrin, bufencarb, buprofezin, butacarb, cadusafos, carbaryl, carbofuran, carbosulfan, cartap, cartap hydrochloride, chlorantraniliprole, chlorfenapyr, chlorfenvinphos, chlorfluazuron, chlormephos, chlorpyrifos, chlorpyrifos-methyl, chromafenozide, clothianidin, cyantraniliprole, cyfluthrin, cyhalothrin, cypermethrin, deltamethrin, diazinon, dicrotophos, diflubenzuron, dimethoate dinotefuran, disulfoton, emamectin, emamectin benzoate, endosulfan, endothion, endrin, EPN, esfenvalerate, etaphos, ethiofencarb, ethion, ethiprole, ethoate-methyl, etofenprox, fenamiphos, fenazaflor, fenethacarb, fenitrothion, fenobucarb, fenpropathrin, fensulfothion, fenthion, fenthion-ethyl, fenvalerate, fipronil, flonicamid, flubendiamide, flucythrinate, fonofos, fufenozide, furathiocarb, gamma-cyhalothrin, gamma-HCH, halfenprox, halofenozide, heptenophos, hyquincarb, imidacloprid, indoxacarb, isazofos, isobenzan, isocarbophos, isofenphos, isofenphos-methyl, isoprocarb, isothioate, isoxathion, kinoprene, lambda-cyhalothrin, lepimectin, lufenuron, malathion, methamidophos, methomyl, methoxyfenozide, mevinphos, mexacarbate, milbemectin, monocrotophos, nitenpyram, novaluron, omethoate, oxamyl, oxydemeton-methyl, oxydeprofos, oxydisulfoton, parathion, parathion-methyl, penfluoron, permethrin, phenthoate, phorate, phosalone, phosfolan, phosmet, phosphamidon, pirimetaphos, pirimicarb, pirimiphos-ethyl, pirimiphos-methyl, primidophos, profenofos, profluthrin, promecarb, propaphos, propoxur, prothiofos, pymetrozine, pyrafluprole, pyridalyl, pyrifluquinazon, pyriprole, pyriproxyfen, spinetoram, spinosad, spirotetramat, sulfoxatlor, sulprofos, tau-fluvalinate, tebufenozide, tebufenpyrad, teflubenzuron, tefluthrin, tetramethylfluthrin, theta-cypermethrin, thiacloprid, thiamethoxam, thicrofos, thiocyclam, thiocyclam oxalate, thiodicarb, thiometon, thiosultap, thiosultap-disodium, thiosultap-monosodium, thuringiensin, tolfenpyrad, triazophos, triflumuron and zeta-cypermethrin.

Suitable fungicides that may be added to the granule of the present invention include tricyclazole, phthalide, carpropamide, pyroquilon, diclocymet, fenoxanil, probenazole, isoprothiolane, iprobenfos, isotianil, tiadinil, kasugamycin, flutolanil, mepronil, pencycuron, polyoxins, validamycin, toclophos-methyl, boscalid, penthiopyrad, thifluzamide, bixafen, fluopyram, isopyrazam, propiconazole, difenoconazole, fenbuconazole, ipconazole, triadimefon, hexaconazole, azoxystrobin, metaminostrobin, orysastrobin, trifloxystrobin and acibenzolar-S-methyl. Some of these fungicides may not be effective for disease control when applied at the timing of an herbicide granule application because fungal disease propagation and growth cycles may not match the targeted weed growth cycles. The effective use and application timing of these fungicides can be easily determined by one of normal skill in the art.

Suitable herbicide safeners that may be added to the granule of the present invention include benoxacor, benthiocarb, cloquintocet-mexyl, daimuron, dichlormid, dicyclonon, dimepiperate, fenchlorazole-ethyl, fenclorim, flurazole, fluxofenim, furilazole, Harpin proteins, isoxadifen-ethyl, mefenpyr-diethyl, mephenate, MG 191, MON 4660, naphthalic anhydride (NA), oxabetrinil, 829148 and N-phenyl-sulfonyl-benzoic acid amides.

Suitable plant growth regulators that may be added to the granule of the present invention include 2,4-D, 2,4-DB, IAA, IBA, naphthaleneacetamide, α-naphthaleneacetic acid, kinetin, zeatin, ethephon, aviglycine, 1-methylcyclopropene (1-MCP), ethephon, gibberellins, gibberellic acid, abscisic acid, ancymidol, flurprimidol, mefluidide, paclobutrazol, tetcyclacis, uniconazole, brassinolide, brassinolide-ethyl and ethylene.

In addition to the compositions and uses set forth above, the present invention also embraces the composition and use of these herbicide granules in combination with one or more additional compatible ingredients which may include, for example, one or more agrochemical active ingredients, plant growth regulators or herbicide safeners, surfactants, dyes, fertilizers and micronutrients, growth regulators and pheromones and any other additional ingredients providing functional utility, such as, for example, stabilizers, fragrants, defoamers and dispersants.

In addition to broadcast application, the granule of the present invention may optionally be diluted in a spray tank containing water carrier and the resulting aqueous mixture used for spray application to control weeds.

When the compositions of the present invention are used in combination with additional active ingredients the presently claimed compositions can be formulated with the additional active ingredient or active ingredients as mixtures of granules, they may be tank mixed with the additional active ingredient or active ingredients for spray application or they may be applied sequentially with the additional active ingredient or active ingredients in separate spray or granule applications.

It is usually desirable to incorporate one or more surface-active agents into the tank mixtures formed with the compositions of the present invention when used in conjunction with the additional active ingredients described herein. Such surface-active agents may advantageously be employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters.

The following examples are presented to illustrate the various aspects of this invention and should not be construed as limitations to the claims.

EXAMPLE 1

Preparation of Granules of the Present Invention

Potassium chloride (KCl) core granules were obtained from Nippon Kayaku Co., Ltd. (Japan) and used as received. Cyhalofop-butyl, methyl soyate and Polyglycol 26-2 (Dow Chemical) are melted together in a flask via a heated water bath controlled at 60-65° C. to give a homogeneous liquid oil phase. Then, the required amount of KCl core granules is added to the liquid oil phase. The KCl core granules and oil phase are mixed thoroughly to ensure uniform absorption of the molten oil phase into the KCl core granules to provide Granule A of Table 1.

TABLE 1

Composition of Granules of the Present Invention

| Ingredients | Granule A Wt % |
|---|---|
| cyhalofop-butyl | 1.8 |
| methyl soyate | 11.5 |
| Polyglycol 26-2 | 0.5 |
| potassium chloride | 86.2 |

EXAMPLE 2

Use of Granules of the Present Invention for Weed Control in Simulated Rice Paddys Simulated Rice Paddy Preparation:
Two kg of mineral soil and 500 ml of distilled water were added to the container (4.163 L (1.1 gallon), 15 cm ht×20.55 cm diameter, HDPE round container; for treatment purposes the surface area is calculated as 331 $cm^2$ with 1 hectare equivalent to $10^8$ $cm^2$) and thoroughly mixed with a spatula for about 5 minutes to create a smooth mud mix. Once the mud is mixed, a 3 cm. furrow is made across the middle of the container to which is added 18 g (0.6 oz.) Osmocote® (registered trademark of The Scotts Company LLC or its affiliates; 17:6:10 N:P:K). The furrow is then sealed keeping the Osmocote®below the surface of the soil.
Plant Propagation
Weed Plant—Chinese sprangletop, *Leptochloa chinensis* (LEFCH): In a small container, 80 grams of mineral soil is mixed with 40 milliliters (mL) of distilled water to make a viscous slurry. ¼ tsp (2-4000) of Leptochloa seed is added to the slurry and thoroughly mixed to evenly distribute the seed. Approximately 3 grams of this slurry is placed atop the prepared mud on one side of each container and spread thinly in a 1-2 cm band across the container. This yields 25-50 plants per pot. Clear shrink wrap is used to cover the containers acting as a terrarium. The wrap is held in place by masking tape until the Leptochloa seed germinates, about 5 days. The covered pots are kept in the greenhouse at a constant temperature of 18 to 22° C. and 50 to 60% relative humidity. Natural light was supplemented with 1000-watt metal halide overhead lamps with an average illumination of 500 microeinsteins (µE) $m^{-2}$ $s^{-1}$ photosynthetic active radiation (PAR). Day length was 16 hours.

Weed Plant—Barnyard grass, *Echinochloa crus-galli* (ECHCG): Once the sprangletop seed has germinated, a shallow depression is made in the mud parallel to the sprangletop. Barnyard grass seed is sprinkled along this trench and then covered with white sand. This yields approximately 20-30 plants per pot. At this stage, the plant material is top-watered with distilled water and kept very moist. Pots are moved to a warmer greenhouse where the temperature is kept at 26 to 28° C. with the same lighting parameters as described for the Chinese sprangletop.

Crop Plant—Paddy rice, *Oryza sativa* subsp. *japonica* var. M202 (ORYSJ): On the same day that the barnyard grass is planted, the rice is also directly seeded into the pot mud following the same methodology. A shallow depression is made in the mud parallel to the Chinese sprangletop and Barnyard grass and the seed is sprinkled along this trench then covered with white sand. This should also yield approximately 5-8 plants per pot.

The plants are allowed to grow until they reach 6-8 cm height in about 8 days.

Flooding and Paddy Application Methods for Herbicide Evaluations

Once the plants have reached the proper size (the growth stage of the various species ranged from 2 to 4 leaves) the containers are flooded with distilled water to a depth of 3 cm leaving 1-2 cm of each plant above the surface. Herbicide treatments are applied directly to the paddy water as granular or liquid formulations at rates adjusted to the surface area. Treatments were replicated 2-3 times. At intervals, percent visual injury and weed control assessments were made on a scale of 0 to 100% compared to the untreated control plants (where 0 is equal to no injury or control and 100 is equal to complete death of the plant).

TABLE 2

Crop Tolerance and Percent Weed Control with Cyhalofop-butyl Granules of the Present Invention 14 days After Application in a Simulated Rice Paddy Trial in the Greenhouse

| Herbicide Active Ingredient (ai) | Treatment Description | Application Rate (g ai/ha) | Average % Injury to Plants[1] | | |
|---|---|---|---|---|---|
| | | | ORYSJ | LEFCH | ECHCG |
| cyhalofop-butyl | Granule A | 45 | 4 | 5 | 0 |
| | | 90 | 4 | 10 | 30 |
| | | 180 | 6 | 65 | 85 |
| | | 360 | 4 | 80 | 100 |
| cyhalofop-butyl | XGA-2444[2] | 45 | 4 | 0 | 0 |
| | | 90 | 4 | 0 | 0 |
| | | 180 | 3 | 43 | 40 |
| | | 360 | 3 | 93 | 33 |
| cyhalofop-butyl | Clincher ® CA[3] | 45 | 0 | 0 | 0 |
| | | 90 | 1 | 0 | 0 |
| | | 180 | 4 | 10 | 25 |
| | | 360 | 5 | 60 | 63 |

[1]ORYSJ = Paddy rice, *Oryza sativa* subsp. *japonica* var. M202
LEFCH = Chinese sprangletop, *Leptochloa chinensis*
ECHCG = Barnyard grass, *Echinochloa crus-galli*
[2]XGA-2444 is a KCl granule formulation containing 18 g/kg of cyhalofop-butyl and 115 g/kg of the petroleum derived adjuvant ditridecyl phthalate (Clincher ® 1KG from Nippon Kayaku Co., Ltd. of Japan)
[3]Clincher ® CA (registered trademark of Dow AgroSciences LLC) is an EC formulation containing 285 grams per liter of cyhalofop-butyl and a petroleum derived adjuvant/solvent.

What is claimed:

1. A herbicide granule composition comprising:
   a) from about 5 grams active ingredient per kilogram (gai/kg) to about 50 gai/kg, with respect to the composition, of an aryloxyphenoxypropionic acid herbicide;
   b) from about 20 g/kg to about 200 g/kg, with respect to the composition, of a non-petroleum derived built-in adjuvant;
   c) from about 700 g/kg to about 950 g/kg, with respect to the composition, a water soluble solid carrier; and
   d) from about 1 g/kg to about 50 g/kg, with respect to the composition, a surfactant;
   wherein the weight ratio of the herbicide to the non-petroleum derived built-in adjuvant is from about 1:3 to about 1:40.

2. The composition of claim 1, wherein the aryloxyphenoxypropionic acid herbicide is cyhalofop-butyl, fenoxaprop-ethyl, fluazifop-P-butyl, haloxyfop-methyl, haloxyfop-R-methyl, metamifop, propaquizafop, quizalofop-P-ethyl, or quizalofop-P-tefuryl.

3. The composition of claim 1, wherein the aryloxyphenoxypropionic acid herbicide is cyhalofop-butyl.

4. The composition of claim 1, wherein the composition comprises from about 10 gai/kg to about 30 gai/kg of the aryloxyphenoxypropionic acid.

5. The composition of claim 1, wherein the non-petroleum derived built-in adjuvant is a water-immiscible organic liquid or solid.

6. The composition of claim 5, wherein the water-immiscible organic liquid or solid is at least one of a plant, algae or animal derived oil or a $C_1$-$C_{10}$ ester of a plant, algae or animal derived oil.

7. The composition of claim 6 in which the $C_1$-$C_{10}$ ester of a plant, algae or animal derived oil is methyl soyate.

8. The composition of claim 1, wherein the composition comprises from about 50 g/kg to about 150 g/kg of the non-petroleum derived built-in adjuvant.

9. The composition of claim 1, wherein the weight ratio of the herbicide to the non-petroleum derived built-in adjuvant is from about 1:4 to about 1:40.

10. The composition of claim 1, wherein the water soluble solid carrier is at least one of an inorganic compound, a lignosulfonate, a carbohydrate, a fertilizer, a water soluble modified cellulose, a natural gum and a synthetic polymer.

11. The composition of claim 1, wherein the water soluble solid carrier is potassium chloride, potassium sulfate, ammonium sulfate, sodium sulfate, calcium carbonate, urea, calcium lignosulfonate or sodium lignosulfonate.

12. The composition of claim 1, wherein the composition comprises about 860 g/kg of the water soluble solid carrier.

13. The composition of claim 1, wherein the surfactant is an alkyl sulfate salt, alkylarylsulfonate salt, alkylphenol-alkylene oxide addition product, soap, alkylnapthalene-sulfonate salt, salt of a dialkyl ester of a sulfosuccinate, sorbitol ester, quaternary amine, polyethylene glycol ester of a fatty acid, block copolymer of ethylene oxide and propylene oxide, salt of a mono or dialkyl phosphate ester, or mixture thereof.

14. The composition of claim 1, wherein:
   (a) the aryloxyphenoxypropionic acid herbicide is cyhalofop-butyl, fenoxaprop-ethyl, fluazifop-P-butyl, haloxyfop-methyl, haloxyfop-R-methyl, metamifop, propaquizafop, quizalofop-P-ethyl, or quizalofop-P-tefuryl;
   (b) the non-petroleum derived built-in adjuvant is a water-immiscible organic liquid or solid;
   (c) the water soluble solid carrier is at least one of an inorganic compound, a lignosulfonate, a carbohydrate, a fertilizer, a water soluble modified cellulose, a natural gum and a synthetic polymer; and
   (d) the surfactant is an alkyl sulfate salt, alkylarylsulfonate salt, alkylphenol-alkylene oxide addition product, soap, alkylnapthalene-sulfonate salt, salt of a dialkyl ester of a sulfosuccinate, sorbitol ester, quaternary amine, polyethylene glycol ester of a fatty acid, block copolymer of ethylene oxide and propylene oxide, salt of a mono or dialkyl phosphate ester, or mixture thereof.

15. The composition of claim 1, wherein the aryloxyphenoxypropionic acid herbicide is cyhalofop-butyl; the non-petroleum derived built-in adjuvant is methyl soyate, the water soluble solid carrier is potassium chloride, and the surfactant is sodium dioctyl sulfosuccinate.

16. The composition of claim 1, wherein the composition further comprises one or more additional pesticides.

17. The composition of claim 1, wherein the composition further comprises one or more herbicide safeners.

18. A method of controlling undesirable vegetation in an aquatic environment which comprises broadcasting or adding the herbicide granule composition of claim 1 into the aquatic environment before emergence or after emergence of the undesirable vegetation.

19. The method of claim 18 in which the aquatic environment is a flooded rice paddy or field.

* * * * *